United States Patent
Borri

(10) Patent No.: US 8,500,445 B2
(45) Date of Patent: Aug. 6, 2013

(54) ORTHODONTIC BRACES

(76) Inventor: Franco Borri, Cossano Canavese (IT)

(*) Notice: Subject to any disclaimer, the term of this patent is extended or adjusted under 35 U.S.C. 154(b) by 18 days.

(21) Appl. No.: 13/289,661

(22) Filed: Nov. 4, 2011

(65) Prior Publication Data
US 2012/0115100 A1 May 10, 2012

(30) Foreign Application Priority Data
Nov. 4, 2010 (IT) .............................. TO2010A0877

(51) Int. Cl.
*A61C 7/00* (2006.01)

(52) U.S. Cl.
USPC ............................................................ 433/18

(58) Field of Classification Search
USPC ................ 433/10, 12, 15–22, 24, 215, 225
See application file for complete search history.

(56) References Cited

U.S. PATENT DOCUMENTS

| 473,040 | A | * | 4/1892 | Wilder ............................ 433/10 |
| 2,086,656 | A | * | 7/1937 | Woodward ........................ 602/5 |
| 3,091,856 | A |   | 6/1963 | Goldstein |
| 3,487,545 | A |   | 1/1970 | Weissman |
| 4,875,856 | A |   | 10/1989 | Grussmark |
| 5,039,303 | A | * | 8/1991 | Irwin .............................. 433/24 |
| 5,683,245 | A | * | 11/1997 | Sachdeva et al. ............... 433/20 |
| 7,306,458 | B1 | * | 12/2007 | Lu ................................. 433/16 |
| 2004/0101801 | A1 | * | 5/2004 | Mao ................................ 433/24 |
| 2007/0218417 | A1 | * | 9/2007 | de Salazar Vinas ............. 433/17 |
| 2010/0124727 | A1 | * | 5/2010 | Shah et al. ...................... 433/19 |

OTHER PUBLICATIONS

Italian Search Report for Application No. TO20100877 mailed Jun. 30, 2011.

* cited by examiner

*Primary Examiner* — Cris L Rodriguez
*Assistant Examiner* — Mirayda A Aponte
(74) *Attorney, Agent, or Firm* — Merchant & Gould P.C.

(57) ABSTRACT

Orthodontic braces include at least one thread 2 and at least one tightener 3, wherein the thread 2 is wound around one or more teeth "D" and is appropriately tensioned by the tightener 3, so as to exert at least one force on the one or more teeth "D" in order to treat malocclusions, labioversions, and mandibular regressions.

8 Claims, 6 Drawing Sheets

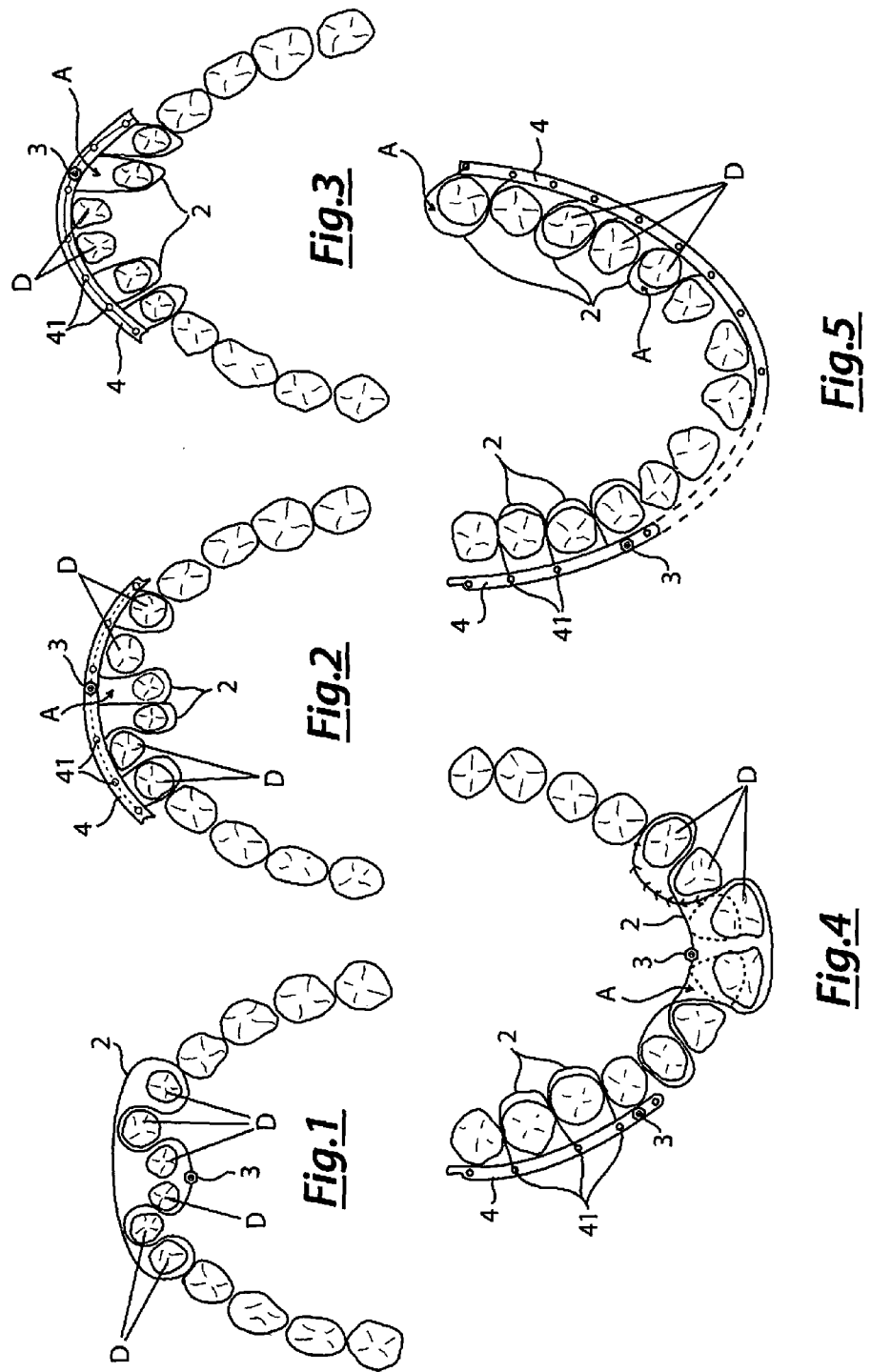

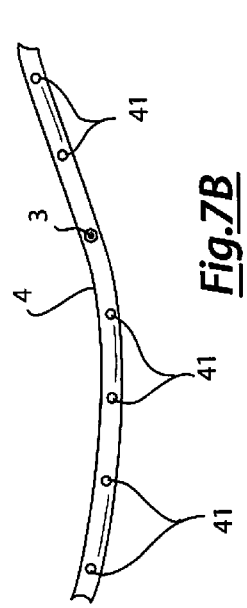
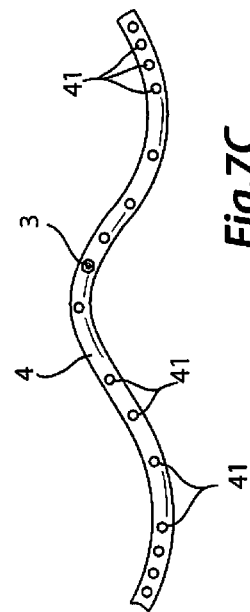
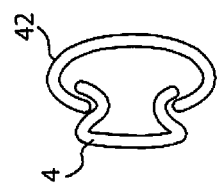
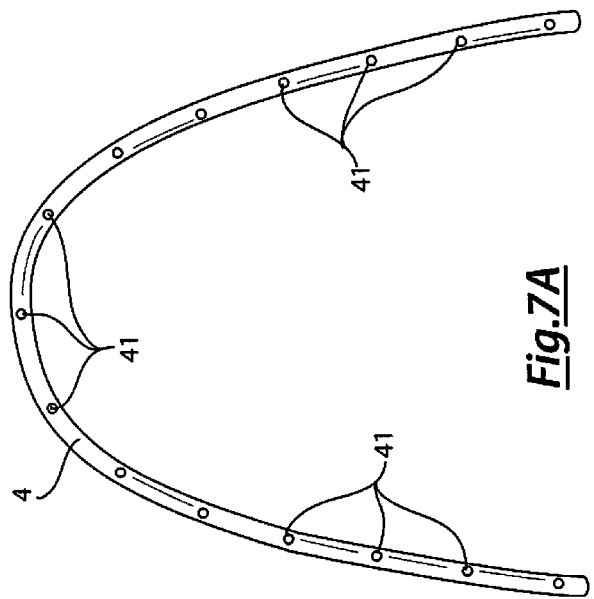
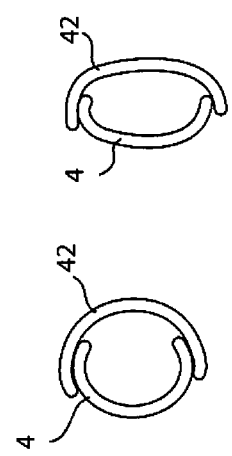

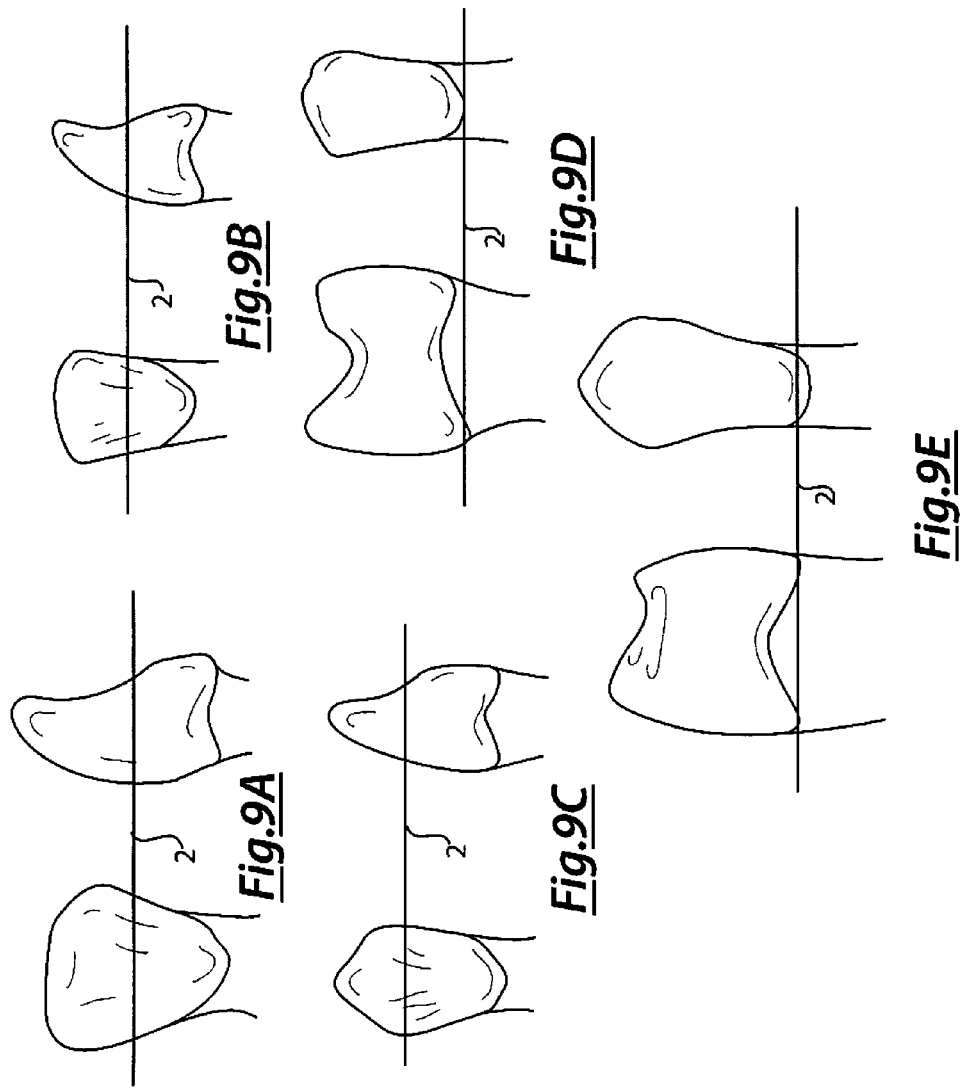

ORTHODONTIC BRACES

This application claims benefit of Serial No. TO 2010 A 000877, filed 4 Nov. 2010 in Italy and which application is incorporated herein by reference. To the extent appropriate, a claim of priority is made to the above disclosed application.

BACKGROUND

The present invention is relative to orthodontic braces for the treatment of dental malocclusions, wherein dental floss is used for the treatment of said malocclusions.

Orthodontic braces are devices used by orthodontic specialists to help align and straighten teeth, in order to obtain a correct mastication, a better dental health as well as a better smile for those people who presents defects and malalignments of the teeth. Normally, orthodontic braces manage to move the teeth in the direction desired.

In the orthodontic industry there are basically three different types of orthodontic braces, i.e. fixed braces, which are used to treat malalignments, since they manage to move the teeth in the direction desired; mobile braces, which are mainly used in interceptive orthodontics to modify wrong habits and behaviors in the growing and developing child; pre-treatment braces, both fixed-type and mobile-type, which perform tasks that could not be otherwise performed with other external orthodontic appliances, such as palate expansion or shaping of the jaw.

Normally, fixed braces comprise wires made of metal material, elastics, bonding materials, tubings or bands on the molars.

Said fixed braces usually comprise threads of different materials and tubings on the molars, thus turning out to be extremely unaesthetic, since they are very showy and, therefore, not suited to be worn by adult patients.

Mobile braces are normally used to treat less serious malocclusions and for dentofacial deformities, but they normally allow limited movements of the teeth. These movements are normally generated by means of screws, springs and arcs.

The braces of this type allow the creation of a harmonious balance in the lower third part of the face both from a functional and from an aesthetic point of view, since they guarantee not only orthodontic results, but also orthopedic results, since they correct and guide the development of the bone bases.

Pre-treatment braces are devices which are sometimes invasive and act on the teeth before the use of one of the above-mentioned types of braces.

The most common type of pre-treatment braces is the one that has to be applied on the palate, which is normally called palatal expander and comprises a palatal metal plaque with a central hole of reduced dimensions, into which a suited expansion key is inserted, which is adapted to obtain the expansion of the palatal plaque.

Fixed braces, as mentioned above, are adapted to treat very serious malocclusions, but they present as a drawback the aesthetic problem.

In order to solve the above-mentioned problems connected with the treatment of malocclusions and the aesthetic aspect, orthodontists normally suggest the use of mobile braces.

Such mobile braces, though, are only adapted to treat minor malocclusions.

If mobile orthodontic braces are used to treat more serious malocclusions, they need much more time in order to reach the desired movements of the teeth; furthermore, as time goes by and the treatment progresses, it is periodically necessary to modify the shape of the braces themselves, often causing an actual replacement of the braces with new ones with a consequent increase of the expenses for the patient.

SUMMARY

The object of the present invention is to solve the above-mentioned problems by providing orthodontic braces, which can be adjusted to any dental arch of any patient and which, by using a dental floss and a tightening device, are able to treat dental malocclusions, labioversions and mandibular retroversions, thus turning out to be substantially invisible and preventing the patient from experiencing problems of verbal distortion.

BRIEF DESCRIPTION OF THE DRAWINGS

The additional features and advantages of said orthodontic braces will be best understood upon perusal of the following detailed description of a specific embodiment with reference to the accompanying drawings, which specifically illustrate what follows:

FIG. 1 shows a top view of a lower dental arch, in which there are applied the braces according to an embodiment, for the tensioning of the mandibular incisors in retroversion, of the present invention;

FIG. 2 shows a top view of the braces according to the present invention in an alternative embodiment, which is adapted to treat retroversions of the mandibular incisors;

FIG. 3 shows, in a top view, braces for the lower arch, which are adapted to treat labioversions of the mandibular incisors;

FIG. 4 shows, in a top view, braces applied to an upper dental arch, which are suited to treat labioversions;

FIG. 5 shows, in a top view, braces applied to an upper dental arch, which are suited to treat malocclusions;

FIG. 7A shows the frame in a top view;

FIG. 7B shows the frame in a lateral view;

FIG. 7C shows the frame in a front view;

FIG. 7D shows different embodiments of the section of the frame;

FIG. 9A shows the positioning of the thread with respect to a central incisor;

FIG. 9B shows the positioning of the thread with respect to a lateral incisor;

FIG. 9C shows the positioning of the thread with respect to a canine tooth;

FIG. 9D shows the positioning of the thread with respect to a premolar;

FIG. 9E shows the positioning of the thread with respect to a molar;

DETAILED DESCRIPTION

Figure 6B:
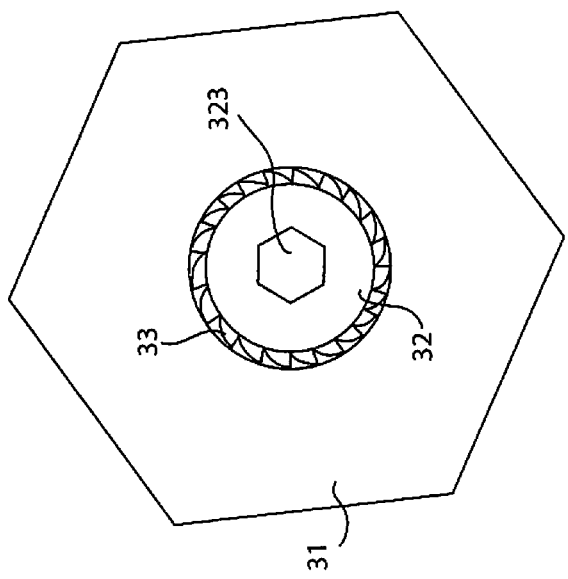
FIG. 6B shows a second lateral view of the tightening means.

With reference to the above-mentioned figures, the orthodontic braces comprise at least one thread 2, preferably a dental floss, and at least one tightening means 3, which is characterized in that said thread 2 is wound around one or more teeth "D", for example by means of a loop "A", and is appropriately tensioned by means of tightening means 3, so as to directly or indirectly exert at least one force on said tooth "D" and preferably also on the neighboring teeth, in order to treat malocclusions, labioversions, and mandibular retroversions.

Said braces comprise, furthermore, at least one sheath portion 21 of rubbery material, into which the thread 2 is inserted and which is adapted to protect at least one portion of thread 2 and to prevent said thread 2 from ending up arranged in the portion of tooth "D" close to the gum.

Said braces comprise, furthermore, at least one frame 4 to be positioned within the oral cavity, preferably between the tooth necks and the gingival arch, which comprises a plurality of holes 41, preferably through holes; said frame preferably presenting an elongated shape and being characterized by a variable stiffness along its length.

Furthermore, on both edges of said holes 41 there is arranged a protection, which is adapted to prevent the thread 2 from getting damaged, for example, due to irregularities in frame 4 generated during the manufacturing of said holes 41.

The stiffness of said frame 4 has to be such as to allow frame 4 itself to adjust to the curvature of the dental arch to be treat; furthermore, said frame 4 has to be sufficiently stiff, at least on one point, so that the force applied for the treatment of tooth "D" does not deform it.

Figure 8B:
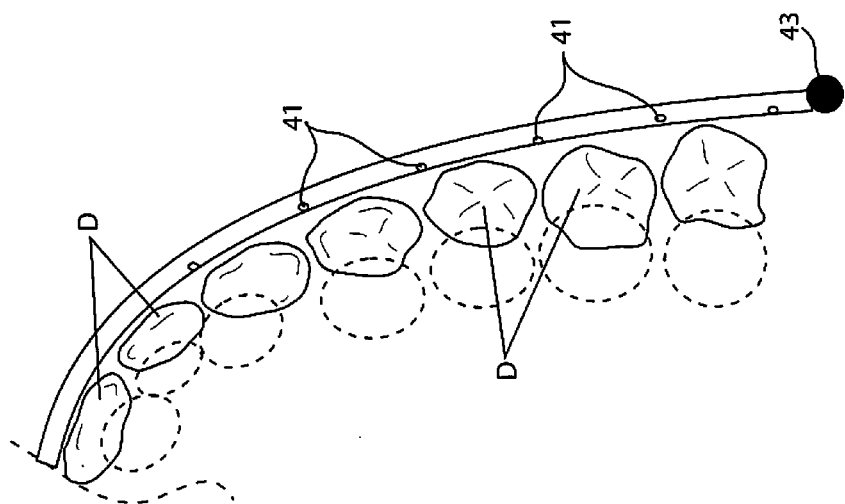
FIG. 8B is a top view of the positioning of the holes on the frame with respect to a dental arch.
Figure 8A:
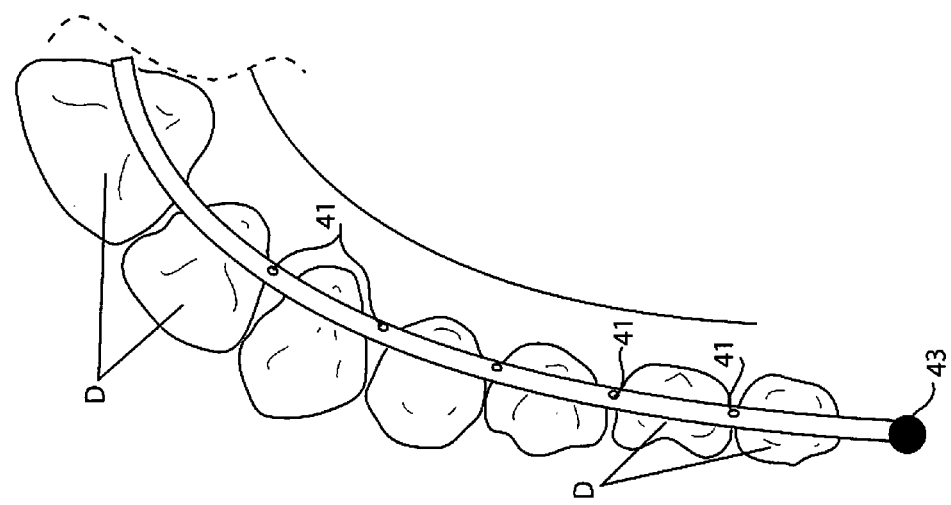
FIG. 8A is a prospective view of the positioning of the holes on the frame with respect to a dental arch.

Said holes 41 are preferably arranged at appropriate distances from one another; for example, they are arranged so as to correspond to the spacing point between the different teeth, as shown in FIG. 8.

As mentioned above, thread 2 is preferably a dental floss normally used for oral hygiene or another type of thread, which is equally adapted to be positioned into the mouth of the patient and presents an adequate resistance to tensioning.

Said thread 2 is made of filaments of materials such as, for example, nylon or plastic.

Said thread 2 is wound around at least one tooth "D", so as to exert at least one force on said tooth "D" or on the neighboring teeth, in order to treat malocclusions, labioversions, and mandibular retroversions.

As shown in FIG. 1, in an embodiment of said braces for the treatment of retroversions of the mandibular central incisors, said thread 2 is preferably wound around the two central incisors, so as to create a loop; both ends are wound, in turn, around the lateral incisors, both left and right, thus displacing the thread from the outside of the oral cavity towards the inside of the oral cavity; finally, said ends are displaced again towards the outside, thus ending up wound around the canine teeth, both right and left.

Thanks to this solution, thread 2 exerts a force on the lateral incisors and on the canine teeth and allows the advancement of the central incisors; furthermore, the force exerted by thread 2 on the lateral incisors and on the canine teeth leads to an increase in the distance between the teeth of the two half-arches, thus leaving space to the central incisors that are displaced from the normal line of occlusion towards the inside.

Figure 10C:
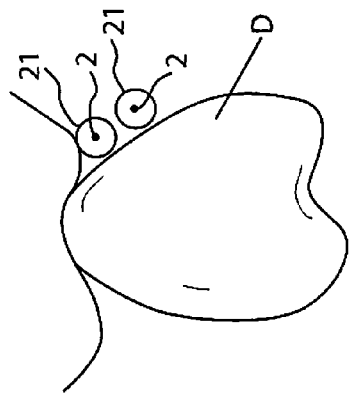
FIG. 10C shows the arrangement of the sheath with respect to the teeth in a sectional view of the sheath applied to a tooth.
Figure 10B:
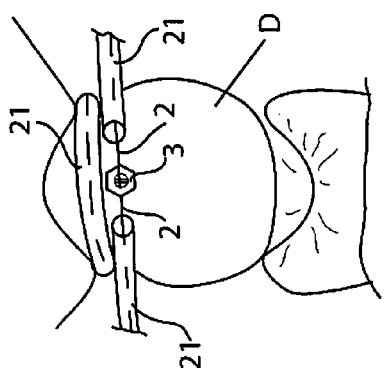
FIG. 10B shows the arrangement of the sheath with respect to the teeth in a lateral view.
Figure 10A:
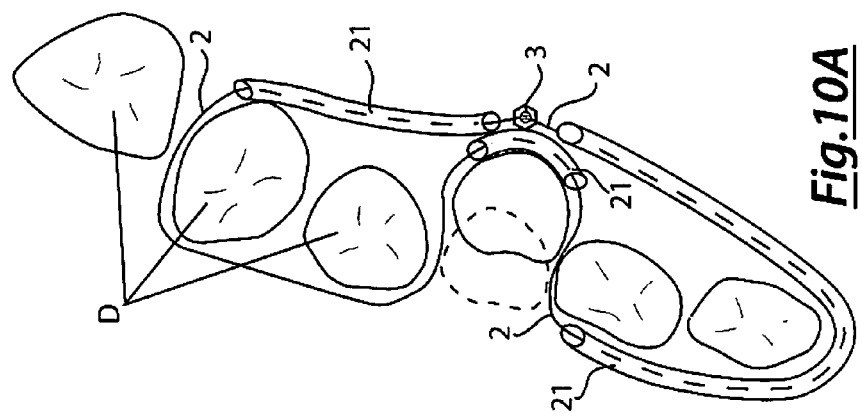
FIG. 10A shows the arrangement of the sheath with respect to the teeth in a top view.

As shown in FIG. 10, it is possible to insert one or more sheath portions 21, which is adapted to protect thread 2 from possible damages caused by the friction of thread 2 against the edge of a tooth "D", which can be sharp.

Furthermore, said sheath 21 prevents the thread from ending up arranged in the gum neck, thus irritating the gums themselves and causing their shrinkage.

This problem mainly occurs in the molars and premolars, ad shown in FIGS. 9D and 9E.

Tightening means 3 is adapted to tension said thread 2, so as to exert a force on tooth "D" to be treated in the desired direction suited for the treatment.

Figure 6C:
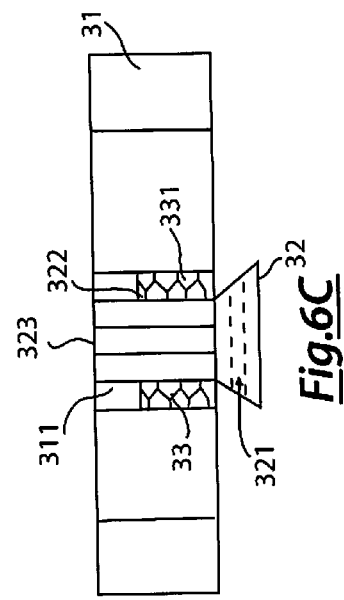
FIG. 6C shows a third lateral view of the tightening means.
Figure 6A:
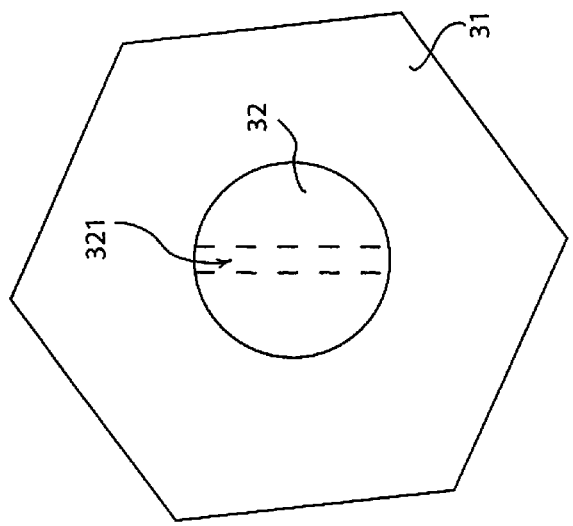
FIG. 6A shows a first lateral view of the tightening means.

In the embodiment shown in FIGS. 6A, 6B and 6C tightening means 3 comprises at least one stabilization portion 31, at least one thread winder 32, and at least one locking device 33.

Stabilization portion 31 preferably is a plate, for example with polygonal shape, which is adapted to house thread winder 32 and locking device 33.

Said portion 31 comprises at least one slot 311, preferably with circular shape, which houses both locking device 33 and thread winder 32. Said thread winder 32, in the embodiment shown, preferably consists of a screw, which comprises a through hole 321, into which thread 2 to be tensioned is inserted.

Said through hole 321 presents an axis that is perpendicular to a longitudinal axis of the screw.

Said thread winder 32, in an embodiment, comprises a first threaded portion 322, which is arranged, for example, on said screw and is preferably right-hand. Locking device 33 is adapted to keep thread winder 32 in the desired position, thus holding thread 2 with the adequate constant tensioning force.

In the embodiment illustrated in FIGS. 6B and 6C, said device preferably comprises a second threaded portion 331 housed in slot 311 of stabilization portion 31.

Said second threaded portion 331 allows thread winder 32 to be screwed, preferably with a clockwise direction of rotation, along said second portion 331 thanks to the first threaded portion 322.

In an alternative embodiment, locking device 33 consists of a gear wheel with asymmetric teeth, which is arranged in slot 311 and blocks the rotation of thread winder 32 in the direction opposite to the direction of rotation, which is preferably clockwise and actuates the tensioning of thread 2.

Said gear wheel allows thread winder 32 to be locked by acting, for example, on at least one tooth comprised in said thread winder 32.

In the embodiment shown in FIGS. 6A, 6B and 6C, said thread winder 32 comprises a hooking portion 323, e.g. a head of a bolt.

Hooking portion 323 allows the execution of the rotation, in the appropriate direction, of tightening means 3 for the tensioning of thread 2, for example by means of a wrench or of an electronic rotating device, which, besides being compatible with hooking portion 323, is able to lock the stabilization portion, so as to allow the rotation of thread winder 32.

Said tightening means 3 is preferably arranged inside the oral cavity, hidden by the dental arch, so as not to be easily visible from the outside.

In case said tightening means 3 cannot be hidden behind the dental arch, the parts constituting said means 3 are made in at least one color that is similar, for example, to the color of the gums or to the color of the dental enamel.

FIG. 9 shows, for each single tooth, the level at which thread 2 would be arranged after it has been wound around teeth "D".

FIG. 2 shows an embodiment comprising frame 4 for the treatment of malocclusions, e.g. lingual regressions of the mandibular central incisors of the arch.

In the embodiment shown in FIGS. 7A, 7B and 7C, frame 4 presents a substantially C-shaped section, in which the hollow portion of the structure is adapted to house thread 2, which runs in said cavity up to chosen hole 41.

The convex portion of the same frame 4 is arranged in direct contact to the dental arch and, as mentioned above, it is preferably positioned between the tooth neck and the gingival arch.

The force exerted by thread 2 allows teeth "D" to be displaced, until they hit frame 4, preferably all teeth "D" comprised in frame 4.

When said teeth "D" hit frame 4, they cannot change any longer their position, since their movement is hindered by frame 4 itself. Said frame 4 comprises, furthermore, at least one covering insert 42, which is adapted to cover said frame 4 once the braces are correctly positioned and tensioned along the dental arches, so as to avoid cuts within the oral cavity.

FIG. 7D illustrates different embodiments of the frame and of covering insert 42 associated thereto.

Furthermore, said frame 4 comprises at least one anti-scratch cap 43, which closes the ends of frame 4, so as to avoid wounds to the oral cavity.

In this embodiment, holes 41 are through holes passing from the hollow portion to the convex portion.

In alternative embodiments, frame 4 has a preferably closed and circular shape, in which all the through holes 41 are parallel.

The position of holes 41 with respect to teeth "D" is not relevant, since, according to the pathology of the patient, the loop of thread 2 is used choosing the most suited holes 41, even though they do not exactly correspond to the gaps between the different teeth "D".

In the embodiment comprising frame 4, tightening means 3 is built-in in frame 4 itself, in which stabilization portion 31 corresponds to a portion of frame 4 itself.

Locking device 33 and thread winder 32 are basically similar to the ones described above.

FIGS. 2, 3, 4 and 5 illustrate different applications, in which there is said frame 4 in different positions, which are suited to treat different malocclusions both for the upper arch and for the lower arch.

As shown in FIG. 2, the braces comprising frame 4 are equally adapted to treat lingual regression and malocclusions of the mandibular front incisors.

This solutions allows a correct alignment of teeth "D" on which said frame 4 acts, since, when all teeth "D" affected by the forces exerted hit frame 4, they cannot advance any further because their movement is hindered by frame 4 itself, whose stiffness does not allow further displacements.

FIG. 3 shows, furthermore, the ability of the braces to treat labioversions of the mandibular front incisors using as a hooking point the lateral incisors an the canine teeth.

The procedure for the correct positioning of the braces according to the present invention comprises the following operating steps:
a) insertion of thread 2 between two holes to generate a loop "A" with known perimeter;
b) positioning of both ends of thread 2 within the concave portion;
c) insertion of said ends within tightening means 3;
d) insertion of the braces in the oral cavity;
e) positioning of frame 4;
f) holding of the braces in position until tightening means 3 renders thread 2 taut;
g) insertion of covering insert 42 and anti-scratch cap 43;
h) in case thread 2 reduces the action on teeth "D", removal of covering insert 42 and of anti-scratch cap 43, and repetition of the operations from step "f" to step "g".

The perimeter of loop "A" is preferably not higher than 20 cm.

The invention claimed is:

1. Orthodontic braces comprising at least one thread and at least one tightening means;
said thread being wound around one or more teeth and tensioned via the tightening means to exert at least one force on said one or more teeth for treating malocclusions, labioversions, and mandibular regressions;
the tightening means comprising at least one stabilization portion, at least one thread winder, and at least one locking device;
wherein the thread winder is implemented via a screw, which comprises a through hole wherein the thread is inserted, which is tensioned via rotation of the thread winder.

2. The braces according to claim 1, wherein the braces comprise at least one frame, to be positioned within an oral cavity between tooth necks and gingival arches, said frame comprising an elongated shape, said frame having a variable stiffness along its length.

3. The braces according to claim 1, wherein the stabilization portion is a plate of polygonal shape which comprises at least one slot, for housing the thread winder and the locking device.

4. The braces according to claim 1, wherein the locking device is adapted to keep the thread winder in a desired position, holding the thread with constant pulling force.

5. The braces according to claim 2, wherein said frame is substantially C-shaped in cross section and comprises at least one covering insert and at least one anti-scratch cap, which are adapted for covering said frame once the braces are positioned and tensioned along the dental arches to prevent causing cuts within the oral cavity.

6. The braces according to claim 1, wherein said braces comprise at least one sheath portion, wherein the thread is inserted, adapted for protection of at least one portion of the thread and for preventing said thread from setting in the portion of tooth proximate the gum.

7. The braces according to claim 1, wherein said thread is dental floss used for oral hygiene.

8. Method for positioning orthodontic braces comprising at least one thread and at least one tightening means; said thread being wound around one or more teeth and tensioned via the tightening means to exert at least one force on said one or more teeth for treating malocclusions, labioversions, and mandibular regressions; the method comprising the following operating steps:
a) inserting the thread between two holes to generate a loop with known perimeter;
b) positioning both ends of the thread within the concave portion;
c) inserting said ends within the tightening means;
d) inserting the braces in the oral cavity;
e) positioning the frame;
f) holding the braces in position until the tightening means renders the thread taut;
g) inserting a covering insert and an anti-scratch cap;
h) wherein the thread reduces action on the teeth, removing the covering insert and the anti-scratch cap, and repeating the operations from step f) to step g).

* * * * *